US00PP21352P2

(12) United States Plant Patent
Noordhuis

(10) Patent No.: US PP21,352 P2
(45) Date of Patent: Sep. 28, 2010

(54) ***LIRIOPE* PLANT NAMED 'EXC 052'**
(50) Latin Name: *Liriope muscari*
Varietal Denomination: EXC 052

(75) Inventor: Bart Noordhuis, Boijl (NL)

(73) Assignee: Eternal Plant Boijl B.V., Boijl (NL)

( * ) Notice: Subject to any disclaimer, the term of this patent is extended or adjusted under 35 U.S.C. 154(b) by 0 days.

(21) Appl. No.: 12/386,663

(22) Filed: Apr. 20, 2009

(51) Int. Cl.
*A01H 5/00* (2006.01)

(52) U.S. Cl. ..... Plt./450

(58) Field of Classification Search ..... Plt./450
See application file for complete search history.

*Primary Examiner*—Annette H Para
(74) *Attorney, Agent, or Firm*—C. A. Whealy

(57) ABSTRACT

A new and distinct cultivar of *Liriope* plant named 'EXC 052', characterized by its compact and outwardly arching plant habit with long and upright inflorescence stalks; freely flowering habit; large violet-colored flowers; and good garden performance.

2 Drawing Sheets

Botanical designation: *Liriope muscari.*
Cultivar denomination: 'EXC 052'.

BACKGROUND OF THE INVENTION

The present invention relates to a new and distinct cultivar of *Liriope* plant, botanically known as *Liriope muscari* and hereinafter referred to by the name 'EXC 052'.

The new *Liriope* plant is a naturally-occurring whole plant mutation of *Liriope muscari* 'Moneymaker', not patented. The new *Liriope* was discovered and selected by the Inventor as a flowering plant from within a population of plants of the parent in a controlled outdoor nursery environment in Boijl, The Netherlands in June, 2005.

Asexual reproduction of the new *Liriope* plant by divisions in a controlled environment in Boijl, The Netherlands since the spring of 2006, has shown that the unique features of this new *Liriope* plant are stable and reproduced true to type in successive generations.

SUMMARY OF THE INVENTION

Plants of the new *Liriope* have not been observed under all possible environmental conditions. The phenotype may vary somewhat with variations in environment and cultural practices such as temperature and light intensity without, however, any variance in genotype.

The following traits have been repeatedly observed and are determined to be the unique characteristics of 'EXC 052'. These characteristics in combination distinguish 'EXC 052' as a new and distinct cultivar of *Liriope:*

1. Compact and outwardly arching plant habit with long and upright inflorescence stalks.
2. Freely flowering habit.
3. Large violet-colored flowers.
4. Good garden performance.

Plants of the new *Liriope* differ from plants of the parent, 'Moneymaker', in the following characteristics:

1. Plants of the new *Liriope* are larger than plants of 'Moneymaker'.
2. Plants of the new *Liriope* have longer inflorescences than plants of 'Moneymaker'.
3. Inflorescences of plants of the new *Liriope* have more flowers than inflorescences of 'Moneymaker'.

4. Plants of the new *Liriope* have darker colored flowers than plants of 'Moneymaker'.
5. Plants of the new *Liriope* are tolerant to lower temperatures than plants of 'Moneymaker'.

Compared to plants of *Liriope muscari* 'Love Potion No. 13', disclosed in U.S. Plant Pat. No. 15,471, plants of the new *Liriope* are more compact, have narrower leaves and are more freely flowering than plants of 'Love Potion No. 13'.

BRIEF DESCRIPTION OF THE PHOTOGRAPHS

The accompanying colored photographs illustrate the overall appearance of the new *Liriope,* showing the colors as true as it is reasonably possible to obtain in colored reproductions of this type. Colors in the photographs may differ slightly from the color values cited in the detailed botanical description which accurately describe the colors of the new *Liriope.*

The photograph on the first sheet comprises a side perspective view of a typical flowering plant of 'EXC 052'.

The photograph on the second sheet is a close-up view of typical inflorescences of 'EXC 052'.

DETAILED BOTANICAL DESCRIPTION

The aforementioned photographs and following observations, measurements and values describe plants grown in Boijl, The Netherlands, under commercial practice during the summer and autumn in an outdoor nursery. Plants were four months old when the photographs and description were taken. During the production of the plants, day temperatures ranged from 15° C. to 25° C. and night temperatures ranged from 10° C. to 15° C. In the following description, color references are made to The Royal Horticultural Society Colour Chart, 2001 Edition, except where general terms of ordinary dictionary significance are used.

Botanical classification: *Liriope muscari* 'EXC 052'.

Parentage: Naturally-occurring whole plant mutation of *Liriope muscari* 'Moneymaker', not patented.

Propagation:

*Type.*—By divisions.

*Time to initiate roots.*—About 15 days at 5° C. to 25° C.

*Time to produce a rooted young plant.*—About 14 to 18 days at 5° C. to 25° C.

*Root description.*—Medium in thickness, fleshy.

*Rooting habit.*—Freely branching; moderately dense.

Plant description:

*Plant form/habit.*—Herbaceous flowering perennial plant; upright plant habit with outwardly arching foliage with upright, strong and long inflorescence stalks. Flowering stems and leaves basal; moderately vigorous growth habit.

*Plant height* (*soil level to top of inflorescences*).—About 40 cm to 50 cm.

*Plant width* (*spread*).—About 40 cm to 50 cm.

Foliage description:

*Arrangement/form.*—Basal rosette, simple, sessile.

*Length.*—About 20 cm to 40 cm.

*Width.*—About 5 mm to 15 mm.

*Shape.*—Lanceolate.

*Apex.*—Obtuse to acute.

*Base.*—Decurrent.

*Margin.*—Entire.

*Texture, upper and lower surfaces.*—Rough, glabrous.

*Venation pattern.*—Parallel.

*Color.*—Developing and fully developed leaves, upper surface: Close to 137A; venation, close to 137B. Developing and fully developed leaves, lower surface: Close to 137C, venation, close to 137B.

Flower description:

*Flower type/habit.*—Numerous single flowers arranged on terminal racemes; flowers face outwardly; freely flowering habit; about 150 to 200 flowers per raceme.

*Fragrance.*—None detected.

*Natural flowering season.*—Continuously flowering from late summer to late autumn in The Netherlands.

*Postproduction longevity.*—Flowers last about eight to ten weeks on the plant; flowers persistent.

*Flower buds.*—Height: About 4 mm to 6 mm. Diameter: About 2 mm to 3 mm. Shape: Oval to obovate. Color: Close to 85B.

*Inflorescence height.*—About 15 cm to 20 cm.

*Inflorescence diameter.*—About 2.5 cm to 3 cm.

*Flower diameter.*—About 5 mm to 8 mm.

*Flower depth.*—About 5 mm to 7 mm.

*Perianth.*—Three inner segments arranged in a single whorl and three outer segments in a single whorl; segments separate. Inner segments: Length: About 5 mm. Width: About 3 mm. Shape: Elliptic. Apex: Obtuse. Margin: Entire. Texture, upper and lower surfaces: Smooth, glabrous. Color: When opening and fully opened, upper surface: Close to N88B, color does not fade with development. When opening and fully opened, lower surface: Close to N88C. Outer segments: Length: About 4 mm to 6 mm. Width: About 2 mm to 3 mm. Shape: Ovate. Apex: Obtuse. Margin: Entire. Texture, upper and lower surfaces: Smooth, glabrous. Color: When opening and fully opened, upper surface: Close to N88D, color does not fade with development. When opening and fully opened, lower surface: Close to N85B.

*Pedicels.*—Length: About 4 mm to 6 mm. Diameter: About 1 mm to 2 mm. Angle: About 90° from the inflorescence stalk. Strength: Weak to moderately strong. Texture: Smooth, glabrous. Color: Close to N87D.

*Reproductive organs.*—Stamens: Quantity per flower: Typically six. Filament length: About 1 mm. Filament color: Close to N87D. Anther shape: Oval. Anther length: About 1 mm to 2 mm. Anther color: Close to 6A. Pollen amount: None observed. Pistils: Quantity per flower: One. Pistil length: About 2 mm. Style length: About 2 mm. Style color: Close to N88B. Stigma shape: Round. Stigma color: Close to N88C. Ovary color: Close to N88B.

*Seeds/fruits.*—Seed and fruit development have not been observed on plants of the new *Liriope*.

Disease/pest resistance: Plants of the new *Liriope* have not been noted to be resistant to pathogens and pests common to *Liriope*.

Garden performance: Plants of the new *Liriope* have been observed to have good garden performance and to tolerate rain, wind and temperatures from about −20° C. to about 30° C.

It is claimed:

1. A new and distinct *Liriope* plant named 'EXC 052' as illustrated and described.

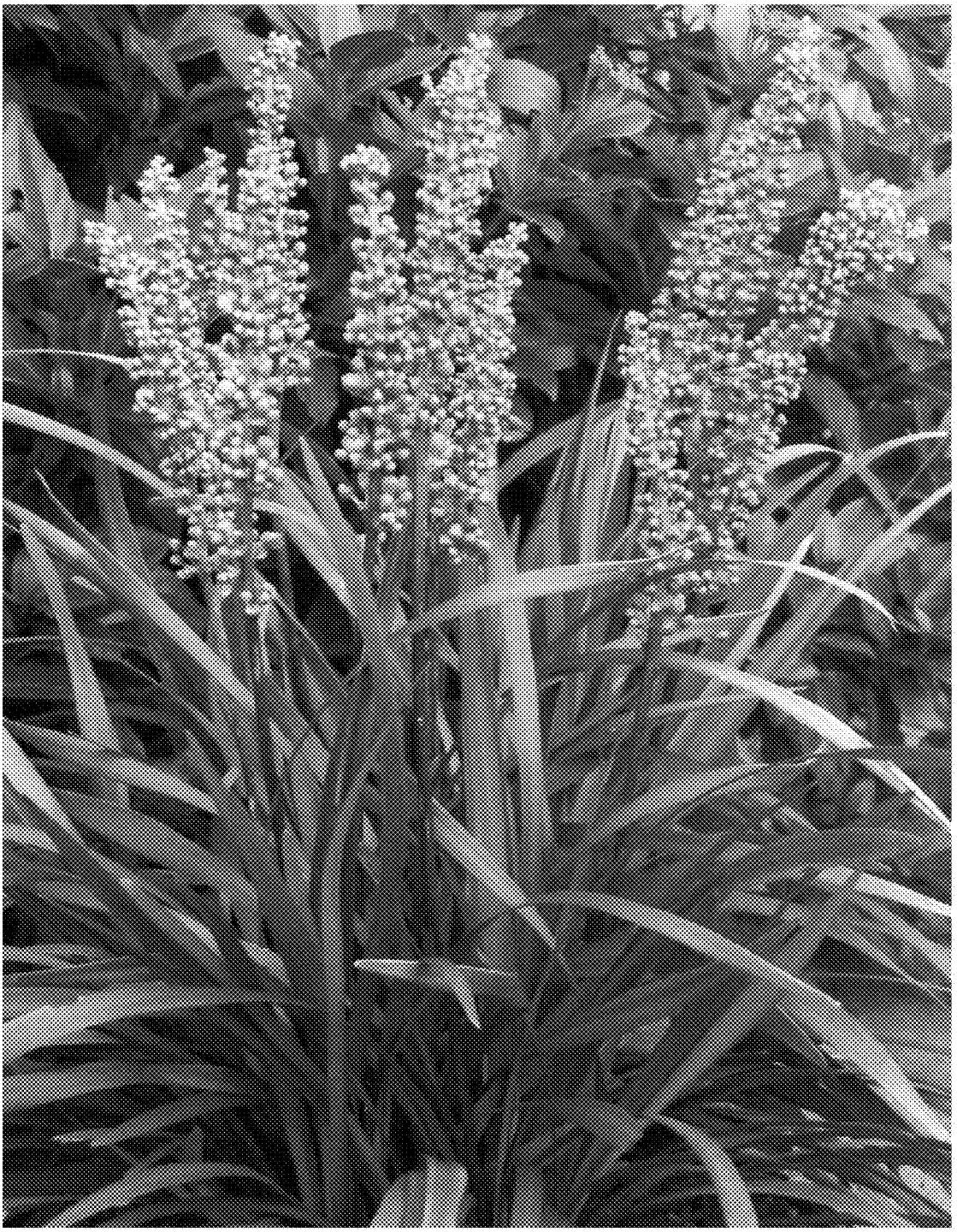

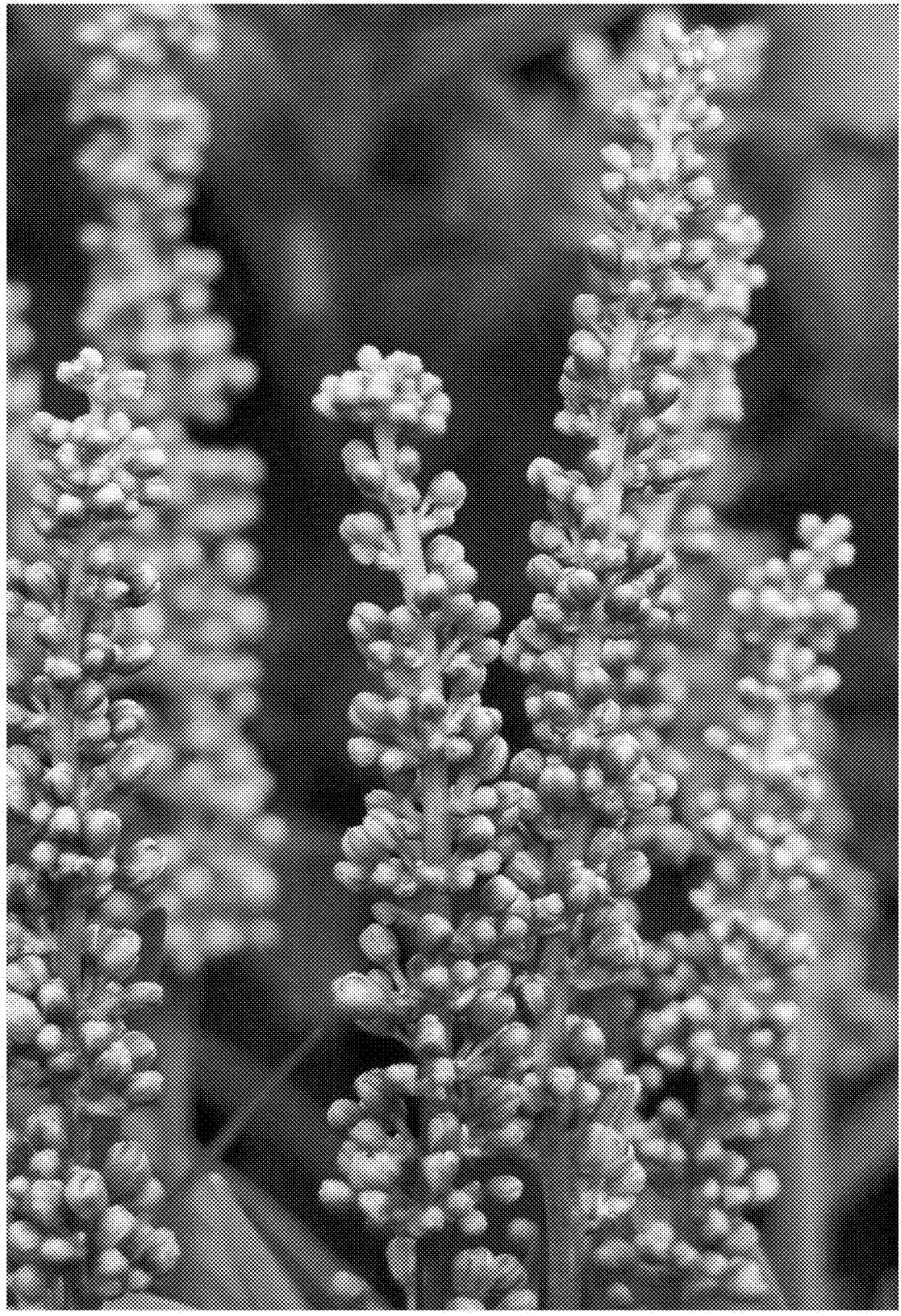

* * * * *